(12) United States Patent
Meeker

(10) Patent No.: US 11,951,321 B2
(45) Date of Patent: *Apr. 9, 2024

(54) PRESSURE RESISTANT CONDUCTIVE FLUID CONTAINMENT

(71) Applicant: WEST AFFUM HOLDINGS DAC, Dublin (IE)

(72) Inventor: Dallas Meeker, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 502 days.

This patent is subject to a terminal disclaimer.

(21) Appl. No.: 17/175,868

(22) Filed: Feb. 15, 2021

(65) Prior Publication Data

US 2021/0236835 A1    Aug. 5, 2021

Related U.S. Application Data

(63) Continuation of application No. 16/389,748, filed on Apr. 19, 2019, now Pat. No. 10,918,878, which is a
(Continued)

(51) Int. Cl.
*A61N 1/39*    (2006.01)
*A61N 1/04*    (2006.01)

(52) U.S. Cl.
CPC .......... *A61N 1/3968* (2013.01); *A61N 1/046* (2013.01); *A61N 1/0492* (2013.01)

(58) Field of Classification Search
CPC ..... A61N 1/3968; A61N 1/046; A61N 1/0492
See application file for complete search history.

(56) References Cited

U.S. PATENT DOCUMENTS 3,724,355 A    4/1973   Unger
4,583,524 A    4/1986   Hutchins
(Continued)

FOREIGN PATENT DOCUMENTS

DE    2005060985 A2    6/2007
EP    2305110 B1    4/2018
(Continued)

OTHER PUBLICATIONS

Zoll, LifeVest, Proven protection from Sudden Cardiac Death, issued Mar. 27, 2018, 4 pages. Pittsburgh PA, USA.
(Continued)

*Primary Examiner* — Joseph M Dietrich
(74) *Attorney, Agent, or Firm* — Christensen O'Connor Johnson Kindness PLLC

(57) ABSTRACT

A conductive fluid reservoir can be used to dispense conductive fluid to increase electrical connectivity between an electrode of a defibrillator and a patient. The reservoir includes a container that holds the conductive fluid, one or more outlets on the container, and an inflatable pouch located at least partially within the container. The inflatable pouch is capable of being inflated from a deflated state to an inflated state. In the deflated state, a free end of the inflatable pouch covers the one or more outlets. In the inflated state, the free end of the inflatable pouch is removed from the one or more outlets such that the conductive fluid is allowed to flow out of the container via the one or more outlets. Inflating the inflatable pouch causes the conductive fluid to be dispensed from the reservoir.

20 Claims, 11 Drawing Sheets

Related U.S. Application Data continuation of application No. 15/798,203, filed on Oct. 30, 2017, now Pat. No. 10,265,535, which is a continuation of application No. 15/213,247, filed on Jul. 18, 2016, now Pat. No. 9,833,631, which is a continuation of application No. 14/523,488, filed on Oct. 24, 2014, now Pat. No. 9,393,437.

(60) Provisional application No. 61/974,070, filed on Apr. 2, 2014.

(56) References Cited

U.S. PATENT DOCUMENTS

| | | |
|---|---|---|
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Hellman et al. |
| 5,228,449 A | 7/1993 | Christ et al. |
| 5,348,008 A | 9/1994 | Bomn et al. |
| 5,353,793 A | 10/1994 | Bomn |
| RE34,800 E | 11/1994 | Hutchins |
| 5,394,892 A | 3/1995 | Kenny |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lysler |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,450,942 B1 | 9/2002 | Lapanashvili et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,753,759 B2 | 7/2010 | Pintor et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 10/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,591,983 B2 | 3/2017 | Amir et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buritonil et al. |
| 2014/0081369 A1 | 3/2014 | Sosa et al. |
| 2014/0163663 A1 | 6/2014 | Poddar et al. |
| 2014/0207201 A1 | 7/2014 | Piha et al. |
| 2014/0213875 A1 | 7/2014 | Freeman et al. |
| 2014/0324112 A1 | 10/2014 | Macho et al. |
| 2014/0378812 A1 | 12/2014 | Saroka et al. |
| 2015/0005588 A1 | 1/2015 | Herken et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |

(56) References Cited

U.S. PATENT DOCUMENTS

| | | |
|---|---|---|
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0319862 A1 | 11/2017 | Foshee, Jr. et al. |
| 2017/0367591 A1 | 12/2017 | Jorgenseon |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |
| 2020/0155826 A1 | 5/2020 | Kaib et al. |

FOREIGN PATENT DOCUMENTS

| | | |
|---|---|---|
| JP | 4320257 B2 | 8/2009 |
| JP | 2014526282 A | 10/2014 |
| JP | 5963767 B2 | 8/2016 |
| WO | 1998039061 A2 | 9/1998 |
| WO | 2011146448 A1 | 11/2011 |
| WO | 2012064604 A1 | 5/2012 |
| WO | 2012151160 A1 | 11/2012 |
| WO | 2015056262 A1 | 4/2015 |

OTHER PUBLICATIONS

International Search Report and Written Opinion for PCT Application No. PCT/US2015/051726, dated May 20, 2016, European Patent Office, 9 pages.

Klein, H. U., Goldenberg I., & Moss, A. J., "Risk Stratification for Implantable Cardioverter Defibrillator Therapy: The Role of the Wearable Cardioverter-Defibrillator," Clinical update, European Heart Jounal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

Heartstart MRx and XL AED Algorithm—Application Note, Jul. 2001, Edition 2 Phillips Healthcare, USA.

Zoll LifeVest Model 4000 Patient Manual PN 20B0047 Rev B, (C) 2009-2012.

Australian Examination report No. 1, dated Feb. 19, 2021, issued in corresponding Australian Application No. 2019240716, filed Sep. 23, 2015, 10 pages.

| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | ✓ | |
| AED | ✓ | ✓ |

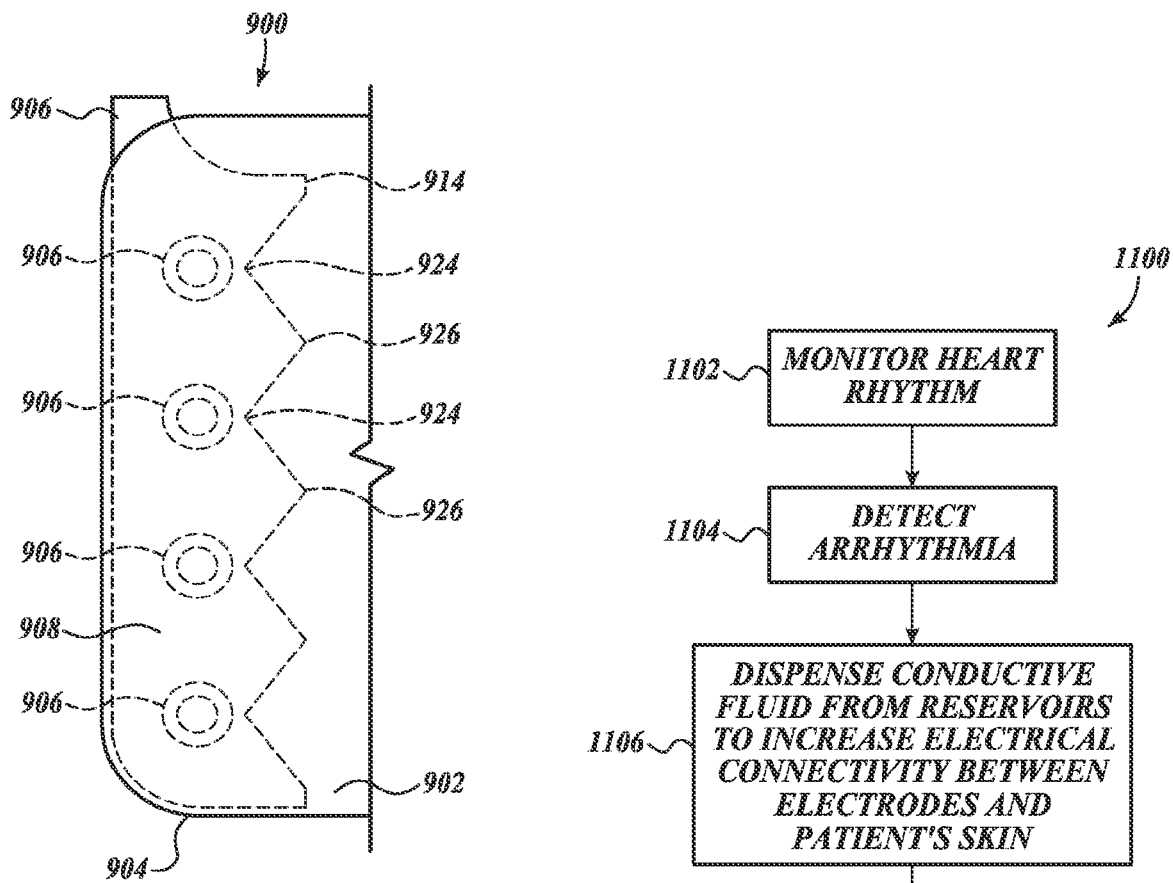
FIG. 9
FIG. 11
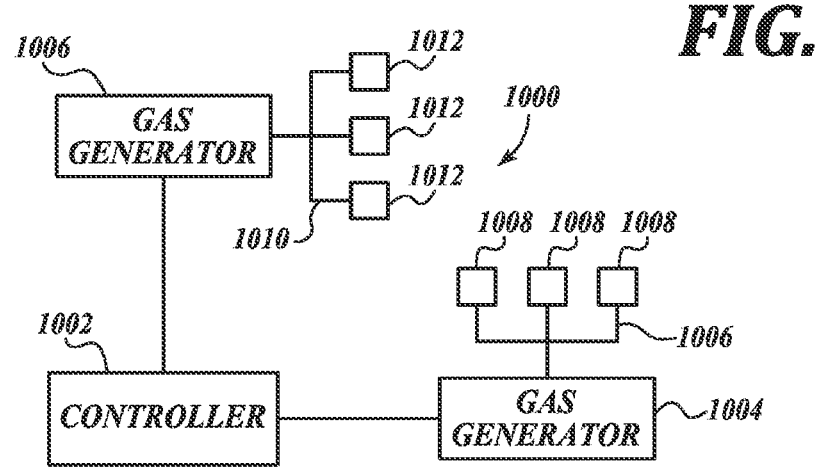
FIG. 10

PRESSURE RESISTANT CONDUCTIVE FLUID CONTAINMENT

CROSS-REFERENCE TO RELATED APPLICATION

This application is a continuation of U.S. patent application Ser. No. 16/389,748, titled PRESSURE RESISTANT CONDUCTIVE FLUID CONTAINMENT and filed Apr. 19, 2019, which is a continuation of U.S. patent application Ser. No. 15/798,203, now issued U.S. patent Ser. No. 10/265,535, titled PRESSURE RESISTANT CONDUCTIVE FLUID CONTAINMENT and filed Oct. 30, 2017, which is a continuation of U.S. patent application Ser. No. 15/213,247, now issued U.S. Pat. No. 9,833,631, titled PRESSURE RESISTANT CONDUCTIVE FLUID CONTAINMENT and filed Jul. 18, 2016, which is a continuation of U.S. patent application Ser. No. 14/523,488, now issued U.S. Pat. No. 9,393,437, titled PRESSURE RESISTANT CONDUCTIVE FLUID CONTAINMENT and filed Oct. 24, 2014, which claims the benefit of U.S. Provisional Patent Application No. 61/974,070, filed Apr. 2, 2014, the contents of which are hereby incorporated by reference in their entirety.

BACKGROUND

External defibrillators are electronic devices that can be used to automatically diagnose and treat patients with particular cardiac problems. External defibrillators typically treat patients through defibrillation, which is a process that delivers an electrical discharge to a patient's heart to stop cardiac arrhythmias. The defibrillation can allow the patient's heart to reestablish an effective rhythm.

Many cardiac conditions that are treatable by external defibrillators can lead to death or serious injury (e.g., brain damage) within minutes of the onset of symptoms if defibrillation is not delivered to the patient. The patient's chances for avoiding death or permanent injury increase as the time between the onset of symptoms and defibrillation treatment decreases. In some cases, the survival rate of patients suffering from cardiac arrhythmia decreases by about 10% for each minute the administration of treatment is delayed, and the survival rate of some patients can be less than 2% after about 10 minutes without treatment.

Some patients have medical conditions that make the patients especially susceptible to needing defibrillation treatment. For example, patients that have recently suffered a heart attack or undergone a heart procedure, such as bypass surgery, may have a higher risk for a life-threatening arrhythmia. Those patients may benefit from the use of a wearable defibrillator. A wearable defibrillator includes a garment that can be worn beneath the patient's clothing. The wearable defibrillator also includes a monitor-defibrillator that constantly monitors the patient's heart for life-threatening heart rhythms and automatically delivers defibrillation treatment to the patient's heart if a life-threatening heart rhythm is detected.

In order to take most advantage of a wearable defibrillator, the components of a wearable defibrillator need to be effective for the time that the patient wears the wearable defibrillator.

Making a wearable defibrillator comfortable for the patient to wear and usable for the length of time that the patient wears the wearable defibrillator increases the likelihood that the patient will be wearing the wearable defibrillator when an arrhythmia develops and that the patient will receive effective treatment for the arrhythmia.

SUMMARY

The following summary is provided to introduce a selection of concepts in a simplified form that are further described below in the Detailed Description. This summary is not intended to identify key features of the claimed subject matter, nor is it intended to be used as an aid in determining the scope of the claimed subject matter.

In at least one embodiment, a system for use with a wearable defibrillator worn by a patient includes an electrode, a source of pressurized fluid (e.g., a pressurized liquid or a pressurized gas), a conductive fluid reservoir, and a controller. The conductive fluid reservoir contains a conductive fluid. The conductive fluid reservoir includes one or more outlets and an inflatable pouch. The controller is configured to control selective delivery of pressurized fluid from the source of pressurized fluid to the inflatable pouch. The inflatable pouch is configured to be inflated from a deflated state to an inflated state in response to pressurized fluid being delivered from the source of pressurized fluid. In the deflated state, a free end of the inflatable pouch covers the one or more outlets. In the inflated state, the free end of the inflatable pouch is removed from the one or more outlets such that the conductive fluid is allowed to flow from the conductive fluid reservoir through the one or more outlets to increase electrical connectivity between the electrode and the patient.

In one example, the conductive fluid reservoir is one of a plurality of conductive fluid reservoirs. The source of pressurized fluid can be coupled to each of the plurality of conductive fluid reservoirs via fluid channels. In another example, the system includes a monitor configured to monitor a heart rhythm of the patient. The controller can be configured to cause pressurized fluid to be delivered from the source of pressurized fluid to the inflatable pouch in response to the monitor detecting an arrhythmia while monitoring the heart rhythm of the patient. In another example, the system includes a defibrillator configured to deliver an electrical discharge to the patient via the electrode and the conductive fluid. In another example, the source of pressurized fluid comprises a gas generator. In yet another example, the system also includes a second electrode, a second source of pressurized fluid, and a second conductive fluid reservoir comprising an inflatable pouch, where the controller is configured to control selective delivery of pressurized fluid from the second source of pressurized fluid to the inflatable pouch of the second conductive fluid reservoir.

In another embodiment, a conductive fluid reservoir includes a container configured to hold a conductive fluid, one or more outlets on the container, and an inflatable pouch located at least partially within the container. The inflatable pouch is capable of being inflated from a deflated state to an inflated state. In the deflated state, a free end of the inflatable pouch covers the one or more outlets. In the inflated state, the free end of the inflatable pouch is removed from the one or more outlets such that the conductive fluid is allowed to flow out of the container via the one or more outlets.

In at least one example, the conductive fluid reservoir includes a seal between the inflatable pouch and the one or more outlets when the inflatable pouch is in the deflated state.

The seal between the inflatable pouch and the one or more outlets is broken when the inflatable pouch is inflated from the deflated state to the inflated state. In another example, the inflatable pouch has a U-shape that includes a first side and a second side. The free end of the inflatable pouch can cover the one or more outlets on the first side of the U-shape. In another example, the inflatable pouch has a ring shape. In another example, the inflatable pouch includes an inlet that protrudes outside of the container, and the inlet is configured to receive pressurized fluid from a source of pressurized fluid. In yet another example, the free end of the inflatable pouch has a saw-tooth shape that includes peaks and valleys, and at least one of the valleys is located near the one or more outlets.

In another embodiment, a method of preparing a patient for defibrillation treatment includes monitoring a heart rhythm of a patient by a monitor, detecting an arrhythmia by the monitor while monitoring the heart rhythm of the patient, and dispensing conductive fluid from a reservoir in response to the monitor detecting the arrhythmia. Dispensing the conductive fluid includes causing pressurized fluid to inflate an inflatable pouch in the reservoir from a deflated state to an inflated state. Inflation of the inflatable pouch from the deflated state to the inflated state causes a free end of the inflatable pouch to be removed from one or more outlets in the reservoir to permit the conductive fluid to flow out of the reservoir via the one or more outlets.

In at least one example, the method further includes delivering, by a defibrillator, an electric charge to the patient via the first electrode and the conductive fluid. In another example, the monitoring includes monitoring the heart rhythm of the patient using a second electrode that is different from the first electrode. In yet another example, causing the pressurized fluid to inflate the inflatable pouch includes one or more of causing a gas generator to generate the pressurized fluid or opening a valve between a source of pressurized fluid and the inflatable pouch.

DESCRIPTION OF THE DRAWINGS

FIG. 9 depicts an embodiment of a free end of an inflatable pouch that can be used with any of the embodiments of inflatable pouches described herein.

FIG. 10 depicts an embodiment of a system that can be used with any of the conductive fluid reservoirs described herein.

FIG. 11 depicts an embodiment of a method for using any of the conductive fluid reservoirs described herein.

DETAILED DESCRIPTION

Wearable defibrillators have electrode pads that can be placed on a patient's skin and deliver an electrical discharge through the patient's skin to the patient's heart. To improve delivery of the electrical discharge through the patient's skin, a conductive fluid (e.g., an electrolyte gel) can be dispensed to increase electrical connectivity between the electrode pads and the patient's skin. Electrolyte gels are typically water-based solutions that include salts (e.g., electrolytes) for electrical conductivity. With non-wearable defibrillators, such as with an automated external defibrillator (AED), an electrode pad can include an adhesive gel that both adheres the electrical pad to the patient's skin and improves electrical connectivity between the electrode pad and the patient's skin.

However, adhesive gel electrode pads are not ideal for use with wearable defibrillators. Over time, the adhesive properties of an adhesive gel electrode pad can deteriorate as the patient wears the electrode pad. The deteriorating adhesive properties of the adhesive gel electrode pad can cause the electrode pad to peel off of the patient's skin, rendering the electrode pad unusable since the electrode pad is no longer properly adhered to the patient. In addition, after the adhesive gel electrode pad had been removed once, the adhesive gel electrode pad will not adhere to the patient's skin as effectively a subsequent time. The contact of an adhesive gel electrode pad to a patient's skin can also cause skin irritation and discomfort over time. Thus, adhesive gel electrode pads are not ideal for wearable defibrillators that are worn by patients over longer periods of time.

Instead of applying a conductive fluid between an electrode and the patient's skin when the patient begins wearing a wearable defibrillator, a conductive fluid can be stored in a reservoir and dispensed to increase electrical connectivity between an electrode of the wearable defibrillator and the patient's skin as needed when the wearable defibrillator prepares to deliver an electrical discharge to the patient. In some wearable defibrillators, the garment portion of the wearable defibrillator includes a conductive material that is positioned between an electrode and the patient's skin. Before the electrode will be used to deliver an electrical discharge to the patient's heart, a conductive fluid can be dispensed to increase electrical connectivity from the electrode through the conductive material to the patient's skin. The conductive fluid can be stored in one or more fluid reservoirs and then be automatically dispensed from the fluid reservoirs by the wearable defibrillator before the wearable defibrillator delivers an electrical discharge to the patient's heart.

Figures 1, 2:
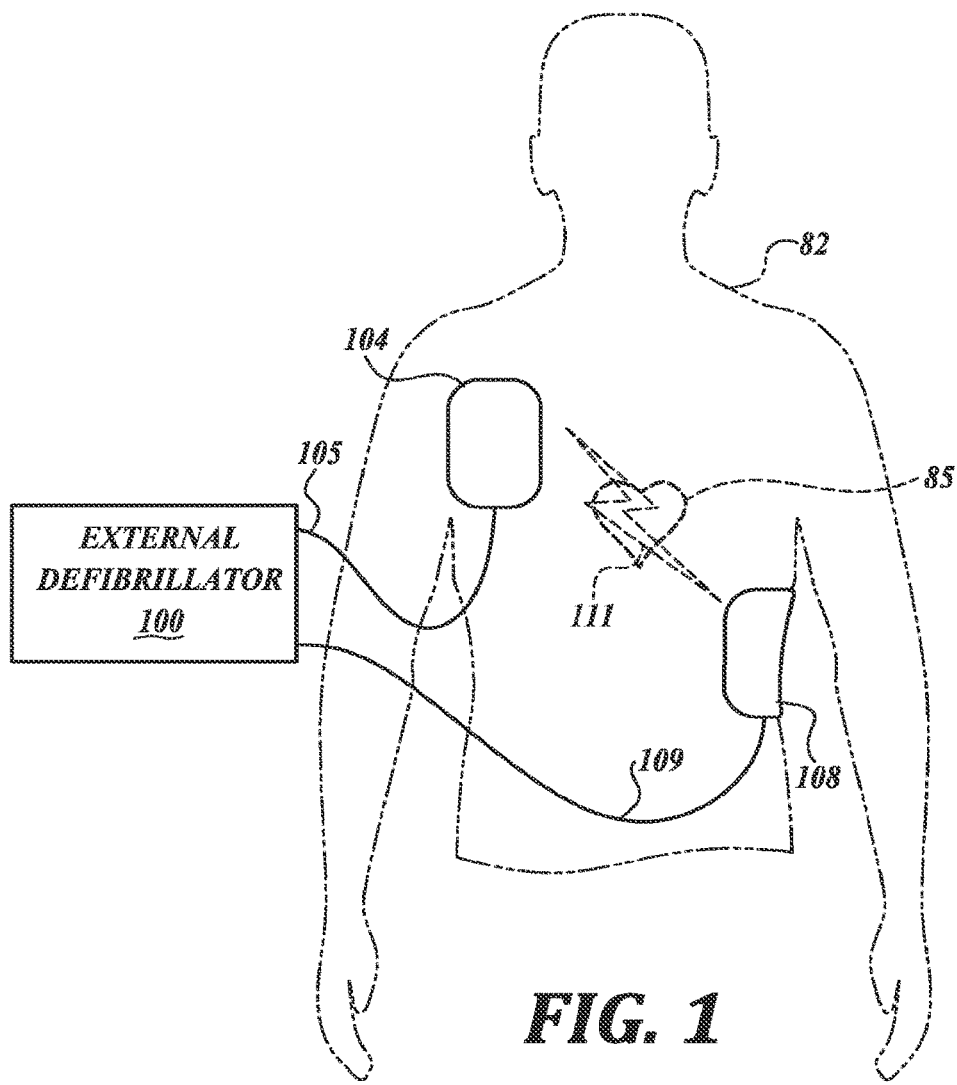
FIG. 1 depicts a diagram of a defibrillation scene.
FIG. 2 depicts a table listing two main types of external defibrillators.

Depicted in FIG. 1 is a diagram of a defibrillation scene. A patient 82 is experiencing a condition in his or her heart 85, which could be, for example, ventricular fibrillation (VF). An external defibrillator 100 has at least two defibrillation electrode pads 104, 108. The electrode pads 104, 108 are coupled to the external defibrillator 100 via respective electrode leads 105, 109. The electrode pads 104, 108 are adhered to the skin of the patient 82. The defibrillator 100 can administer, via the electrode leads 105, 109 and the electrode pads 104, 108, a brief, strong electric discharge 111 through the body of the patient 82. The discharge 111, also known as a defibrillation shock, goes through the patient's heart 85, in an attempt to restart it, for saving the life of the patient 82.

The defibrillator 100 can be one of many different types of defibrillators, each with different sets of features and capabilities. The set of capabilities of the defibrillator 100 is determined by planning who is likely to use it and what training they would likely have.

Examples are now described.

FIG. 2 is a table listing two main types of external defibrillators and who they are primarily intended to be used by. A first type of defibrillator 100 is generally called a defibrillator-monitor, because it is typically formed as a single unit in combination with a patient monitor. A defibrillator-monitor is also sometimes called a monitor-defibrillator. A defibrillator-monitor is generally intended to be used by persons in the medical professions, such as doctors, nurses, paramedics, emergency medical technicians, etc. Such a defibrillator-monitor is intended to be used in a pre-hospital or hospital scenario. In the case of a wearable defibrillator-monitor, a medical professional can fit the wearable defibrillator-monitor on the patient and/or instruct the patient how to wear the wearable defibrillator-monitor such that the patient can have the benefit of the wearable defibrillator-monitor while having the freedom to leave a medical treatment facility.

As a defibrillator, the device 100 can be one of different varieties, or even versatile enough to be able to switch among different modes that individually correspond to the different varieties. One variety is that of an automated defibrillator that can determine whether treatment by way of an electrical discharge is needed and, if so, charge to a predetermined energy level and instruct the user to administer the discharge.

As a patient monitor, the device 100 has features that are additional to what is minimally needed for mere operation as a defibrillator. These features can be used for monitoring physiological indicators of a person in an emergency scenario. These physiological indicators are typically monitored as signals. For example, these signals can include a person's full electrocardiogram (ECG) signals, a subset of the ECG signals, and/or an impedance between two electrodes placed on a person. Additionally, the monitored signals can represent the person's temperature, a noninvasive blood pressure (NIBP), an arterial oxygen saturation through pulse oximetry (SpO2), a concentration or partial pressure of carbon dioxide in the respiratory gases (capnography), and so on. These signals can be further stored and/or transmitted as patient data.

There are additional types of external defibrillators that are not listed in the table in FIG. 2. For example, hybrid defibrillators and/or wearable defibrillators are not listed. Hybrid defibrillators can have aspects of an AED and a defibrillator-monitor. A usual such aspect is additional ECG monitoring capability.

Figure 3:
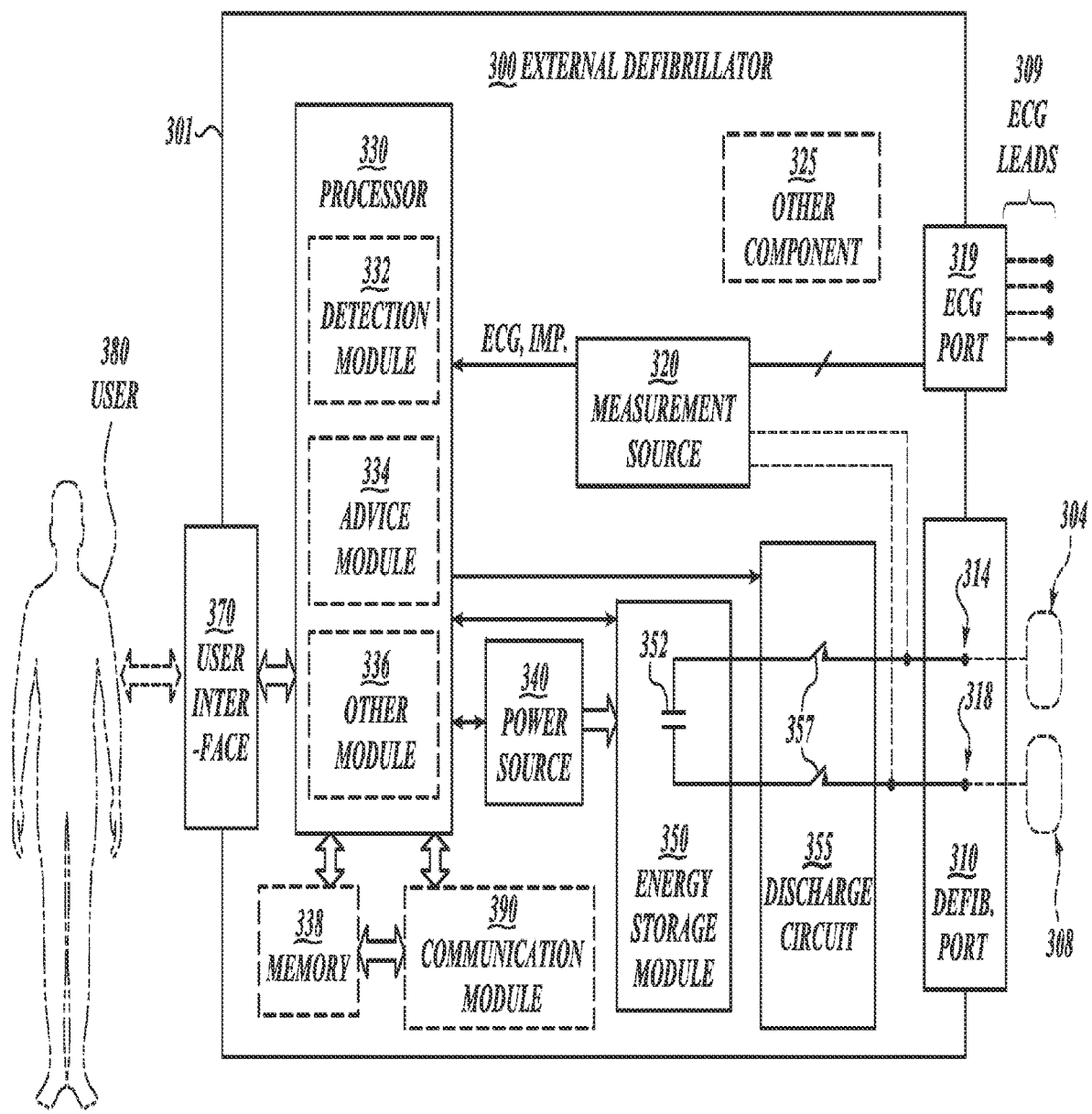
FIG. 3 depicts a diagram showing components of an example of an external defibrillator.

FIG. 3 is a diagram showing components of an external defibrillator 300 made according to embodiments of the present disclosure. These components can be employed, for example, in the external defibrillator 100 of FIG. 1. The components of FIG. 3 can be provided in a housing 301, which is also known as a casing.

The external defibrillator 300 typically includes a defibrillation port 310, such as a socket in housing 301. The defibrillation port 310 includes nodes 314, 318. Defibrillation electrode pads 304, 308, which can be similar to the electrode pads 104, 108 shown in FIG. 1, can be plugged into the defibrillation port 310 so as to make electrical contact with nodes 314, 318, respectively. It is also possible that the electrode pads 304, 308 can be connected continuously to the defibrillation port 310. Either way, the defibrillation port 310 can be used for providing a discharge of electrical energy that has been stored in the defibrillator 300 to the patient 82 via the electrode pads 304, 308, as will be discussed later herein.

If the defibrillator 300 is a defibrillator-monitor, as described with reference to FIG. 2, then it can also have an ECG port 319 in the housing 301 for plugging in ECG leads 309. The ECG leads 309 are usable to sense an ECG signal, e.g., a 12-lead signal, or an ECG signal from a different number of leads. A defibrillator-monitor could have additional ports (not shown) and another component 325. In at least one embodiment, the other component 325 may be structured to filter the ECG signal, e.g., by applying at least one filter to the ECG signal so as to remove chest compression artifacts resulting from chest compressions being delivered to the patient 82.

The defibrillator 300 may also include a measurement source 320 that could be a circuit. The measurement source 320 receives physiological signals from the ECG port 319, and also from other ports, if provided. These physiological signals are sensed and information about the physiological signals is rendered by measurement source 320 as data or other signals.

If the defibrillator 300 is an AED, it may lack the ECG port 319. In such an embodiment however, the measurement source 320 can obtain physiological signals through the nodes 314, 318 instead, when the defibrillation electrode pads 304, 308 are attached to the patient 82. In this case, a person's ECG signal can be sensed as a voltage difference between the electrode pads 304, 308. Additionally, impedance between the electrode pads 304, 308 can be sensed for detecting, among other things, whether the electrode pads 304, 308 have been inadvertently disconnected from the person.

The defibrillator 300 also includes a processor 330. Processor 330 may be implemented in any number of ways for causing actions and operations to be performed. The processor 330 may include, by way of example and not of limitation, digital and/or analog processors such as microprocessors and digital-signal processors (DSPs); controllers such as microcontrollers; software running in a programmable machine; programmable circuits such as Field Programmable Gate Arrays (FPGAs), Field-Programmable Analog Arrays (FPAAs), Programmable Logic Devices (PLDs), Application Specific Integrated Circuits (ASICs), or any combination of one or more of these.

The processor 330 can be considered to have a number of modules. One such module can be a detection module 332 configured to sense outputs of the measurement source 320. The detection module 332 can include a VF detector, for example. Thus, the patient's sensed ECG can be used by the detection module 332 to determine whether the patient is experiencing VF.

Another such module in the processor 330 can be an advice module 334 configured to determine and provide advice based on outputs of the detection module 332. The advice module 334 can include a Shock Advisory Algorithm, implement decision rules, and so on. The advice can be to shock, to not shock, to administer other forms of therapy, and so on. If the advice is to shock, some external defibrillator embodiments merely report that to a user 380 and prompt the user 380 to initiate the shock. Other embodiments automatically execute the advice, by administering the shock. If the advice is to administer CPR, the defibrillator 300 may further issue prompts to the user 380, and so on.

The processor 330 can include additional modules, such as module 336 that provide other functions. In addition, if one or more other components 325 are indeed provided, the component(s) 325 may be operated in part by the processor 330.

The defibrillator 300 optionally further includes a memory 338 that can work together with the processor 330. The memory 338 may be implemented in any number of ways. The memory 338 may include, by way of example and not of limitation, nonvolatile memories (NVM), read-only memories (ROM), random access memories (RAM), any combination of these, and so on. The memory 338, if provided, can include programs to be executed by the processor 330 or the modules therein. The programs can be operational for the inherent needs of the processor 330, and can also include protocols and algorithms for modules such as the advice module 334 to make decisions. In addition, the memory 338 can store prompts for the user 380, etc. Moreover, the memory 338 can store patient data.

The defibrillator 300 may also include a power source 340. To enable portability of the defibrillator 300, the power source 340 typically includes a battery. Such a battery is typically implemented as a battery pack that can be rechargeable or non-rechargeable. Sometimes, a combination of rechargeable and non-rechargeable battery packs is used. Other embodiments of the power source 340 can include an AC power override, for instances where AC power will be available, and so on. In some embodiments, the power source 340 is controlled by the processor 330.

The defibrillator 300 additionally includes an energy storage module 350. The energy storage module 350 is where electrical energy is stored when the defibrillator 300 is preparing to administer a shock through a sudden discharge of energy. The energy storage module 350 can be charged from power source 340 to hold a desired amount of energy, as controlled by the processor 330. In typical implementations, the energy storage module 350 includes one or more capacitors 352 to store and discharge the energy.

The defibrillator 300 further includes a discharge circuit 355. The discharge circuit 355 can be controlled by the processor 330 to permit the energy stored in the energy storage module 350 to be discharged through the nodes 314, 318 to the defibrillation electrode pads 304,308. The discharge circuit 355 can include one or more switches 357 to control the discharge. The switches 357 can be implemented in a number of ways, such as by an H-bridge circuit, and so on.

The defibrillator 300 further includes a user interface 370 for the user 380. The user 380 can be a rescuer or a patient. The user interface 370 can be implemented in any number of ways. For example, the user interface 370 may include a screen to display what is detected and measured, provide visual feedback or prompts to a rescuer to aid their resuscitation attempts, and so on. The user interface 370 may also include a speaker to issue voice prompts, and various controls, such as pushbuttons, keyboards, and so on. CPR prompts, for example, can be issued, visually or by sound, to the rescuer to help the user administer CPR to the patient. Examples of CPR-prompting technology are taught in U.S. Pat. Nos. 6,334,070 and 6,356,785. In addition, the discharge circuit 355 can be controlled by the processor 330.

The defibrillator 300 can optionally include other components. For example, a communication module 390 may be provided for communicating with other machines or devices. Such communication can be performed wirelessly (e.g., by RF or infrared communication), or via wire connections. Data can be communicated, such as patient data, incident information, therapy attempted, CPR performance, and so on, to other machines or devices for further evaluation and/or processing.

Figure 4:
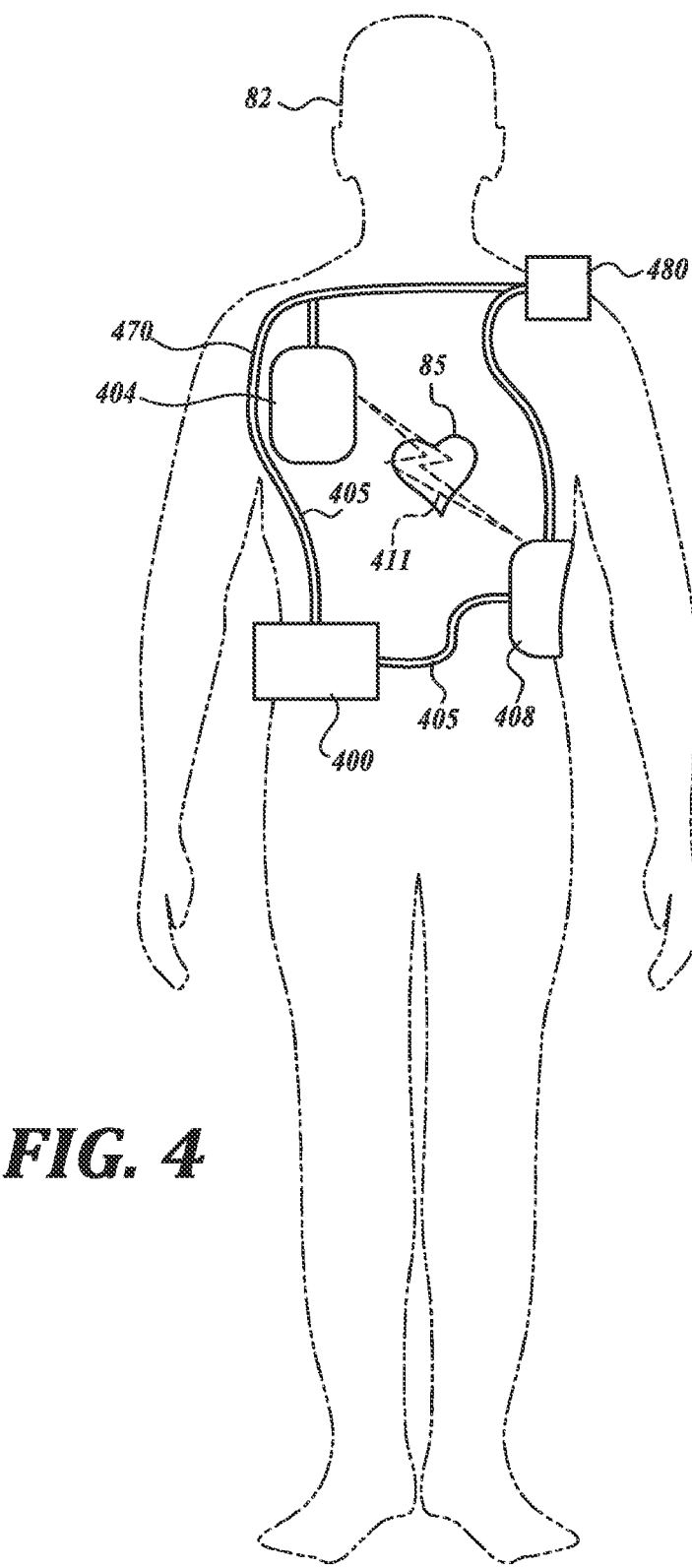
FIG. 4 depicts an embodiment of components of a wearable defibrillator system.

FIG. 4 depicts an embodiment of components of a wearable defibrillator system as might be worn by the patient 82 depicted in FIG. 1. Patient 82 may also be referred to as person 82 and/or wearer 82 since he or she wears components of the wearable defibrillator system.

In FIG. 4, a generic support structure 470 is shown relative to the body of person 82, and thus also relative to his or her heart 85. Structure 470 could be a harness, a vest, one or more belts, or a garment as per the above, and could be implemented in a single component or multiple components, and so on. Structure 470 is wearable by person 82, but the manner of wearing it is not depicted, as structure 470 is depicted only generally in FIG. 4.

A wearable defibrillator system is configured to provide a therapy to a patient by delivering electrical energy to the patient's body in the form of an electric discharge that may be conveyed in one or more pulses. FIG. 4 shows one example of an external defibrillator 400 and defibrillation electrodes 404, 408 that are coupled to the external defibrillator 400 via electrode leads 405. Alternative to the electrode positioning shown in FIG. 4, the electrodes 404, 408 can be positioned anterior and posterior about the body, substantially parallel to each other, and superimposing the heart. Defibrillator 400 and defibrillation electrodes 404, 408 are coupled to support structure 470. As such, all components of defibrillator 400 can therefore be coupled to support structure 470. When defibrillation electrodes 404, 408 make good electrical contact with the body of person 82, defibrillator 400 can administer, via electrodes 404, 408, a brief, strong electric discharge 411 through the body. Discharge 411, also known as a defibrillation shock or therapy shock, is intended to go through the heart 85 and restart the heart 85 in an effort to save the life of person 82. Discharge 411 can also be one or more pacing pulses, and so on.

The wearable defibrillator system may optionally include an outside monitoring device 480. Device 480 is called an "outside" device because it is provided as a standalone device not within the housing of defibrillator 400. Device 480 is configured to monitor at least one local parameter. A local parameter can be a parameter of patient 82, or a parameter of the wearable defibrillation system, or a parameter of the environment, as will be described later herein. Optionally, device 480 is physically coupled to support structure 470. In addition, device 480 can be communicatively coupled with other components that are coupled to support structure 470. Such a component can be a communication module, as will be deemed applicable by a person skilled in the art in view of this disclosure.

Figure 5A:
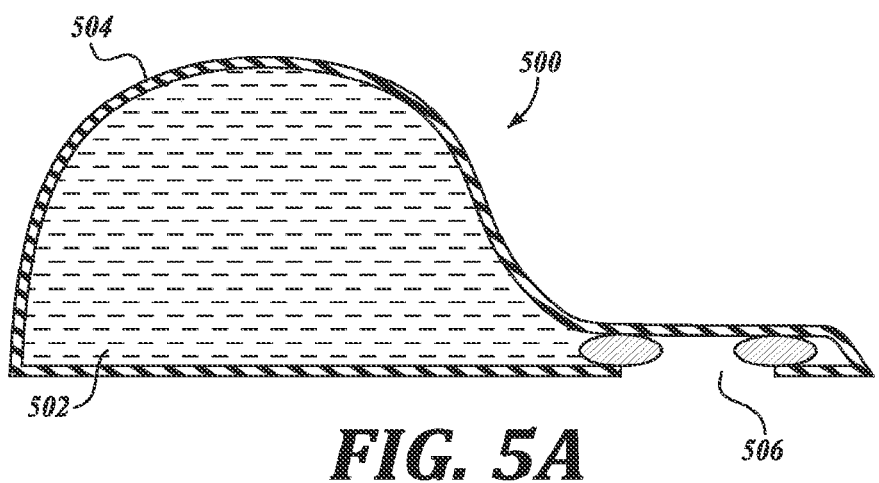
FIGS. 5A to 5C depict cross-sectional views of an embodiment of a traditional conductive fluid reservoir.
Figure 5B:
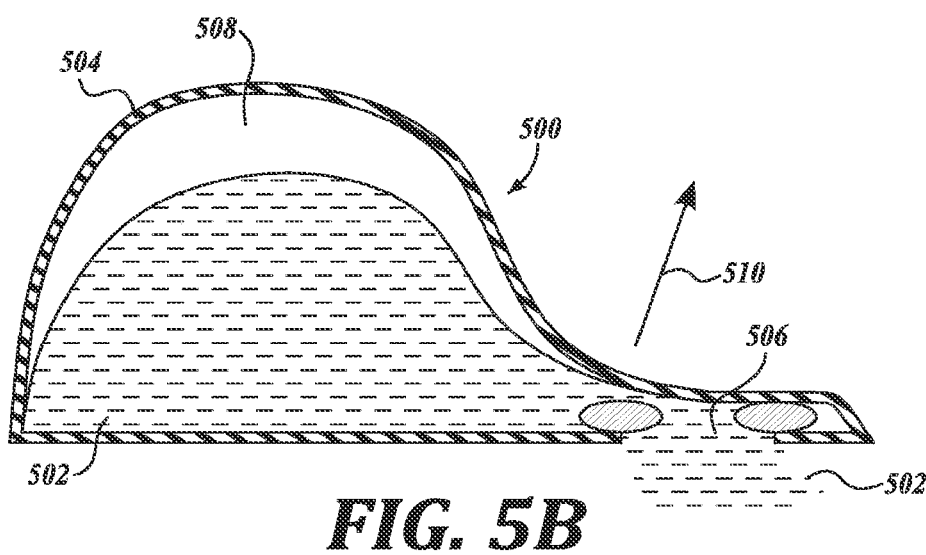
Figure 5C:
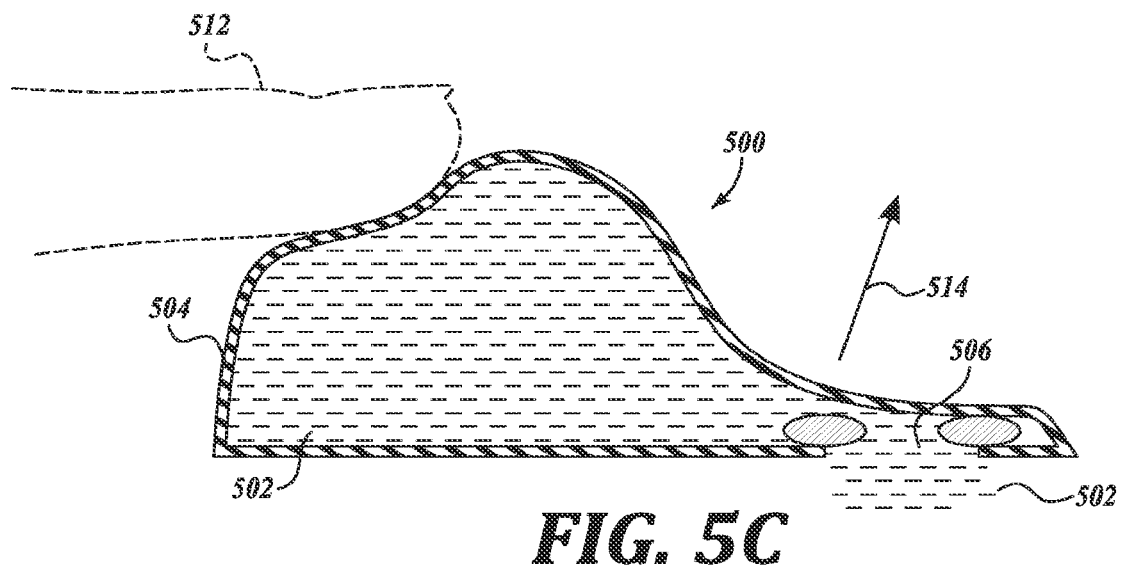

FIGS. 5A to 5C depict cross-sectional views of an embodiment of a traditional conductive fluid reservoir 500 that is usable in a wearable defibrillator system as shown in FIG. 4. The reservoir 500 contains a conductive fluid 502 within a flexible container 504. The reservoir 500 includes one or more outlets 506 through which the conductive fluid 502 can flow. As shown in FIG. 5A, a portion of the flexible container 504 can be normally positioned to cover the one or more outlets 506. In this configuration, the flexible container 504 seals the one or more outlets 506 to hold the conductive fluid 502 within the reservoir 500.

Some or all of the conductive fluid 502 can be dispensed from the reservoir 500 by inflating an inflatable pocket 508 of the flexible container 504. As shown in FIG. 5B, as the inflatable pocket 508 is inflated, and an upward force 510 lifts a portion of the flexible container 504 above the one or more outlets 506. The upward force 510 on the flexible container 504 lifts the flexible container 504 and uncovers the one or more outlets 506, allowing the some or all of the conductive fluid 502 to flow out of the reservoir 500 via the one or more outlets 506. The inflation of the inflatable pocket 508 also exerts a pressure on the conductive fluid 502 to force the conductive fluid 502 out of the one or more outlets 506.

One drawback to the reservoir 500 is depicted in FIG. 5C. As shown in FIG. 5C, an object 512 (e.g., a person's finger) can apply a force to the flexible container 504. The force from the object 512 can be inadvertent, such when a user accidentally pushes on the flexible container 504 or when the patient wearing the wearable defibrillator accidentally bumps into an object. The force caused by the object 512 on the flexible container 504 results in an upward force 514 lifting the flexible container 504 away from the one or more outlets 506. The upward force 514 uncovers the flexible container 504 from the one or more outlets 506 and allows the some or all of the conductive fluid 502 to flow out of the reservoir 500 via the one or more outlets 506.

If the force 512 is an unintended force, the result is unintended dispensing of the conductive fluid 502 via the one or more outlets 506. To a patient wearing the wearable defibrillator, the unintended dispensing of the conductive fluid 502 can cause the patient to think that the wearable defibrillator is defective (e.g., it has a leak). In addition, such unintended dispensing of the conductive fluid 502 is at best an annoyance to the user because of the mess of the dispensed conductive fluid 502, and at worst renders the wearable defibrillator incapable of effectively applying an electrical charge to the patient's skin. Some efforts to address this issue have been made by surrounding the pouch 500 in a rigid container (e.g., a stiff foam); however, such rigid housings make the wearable defibrillator less comfortable to the patient and decrease patient compliance in wearing the defibrillator. Moreover, a rigid housing may not permit the electrode to bend along a contour of the patient's skin, reducing the contact area between the electrode and the patient's skin.

Figure 5D:
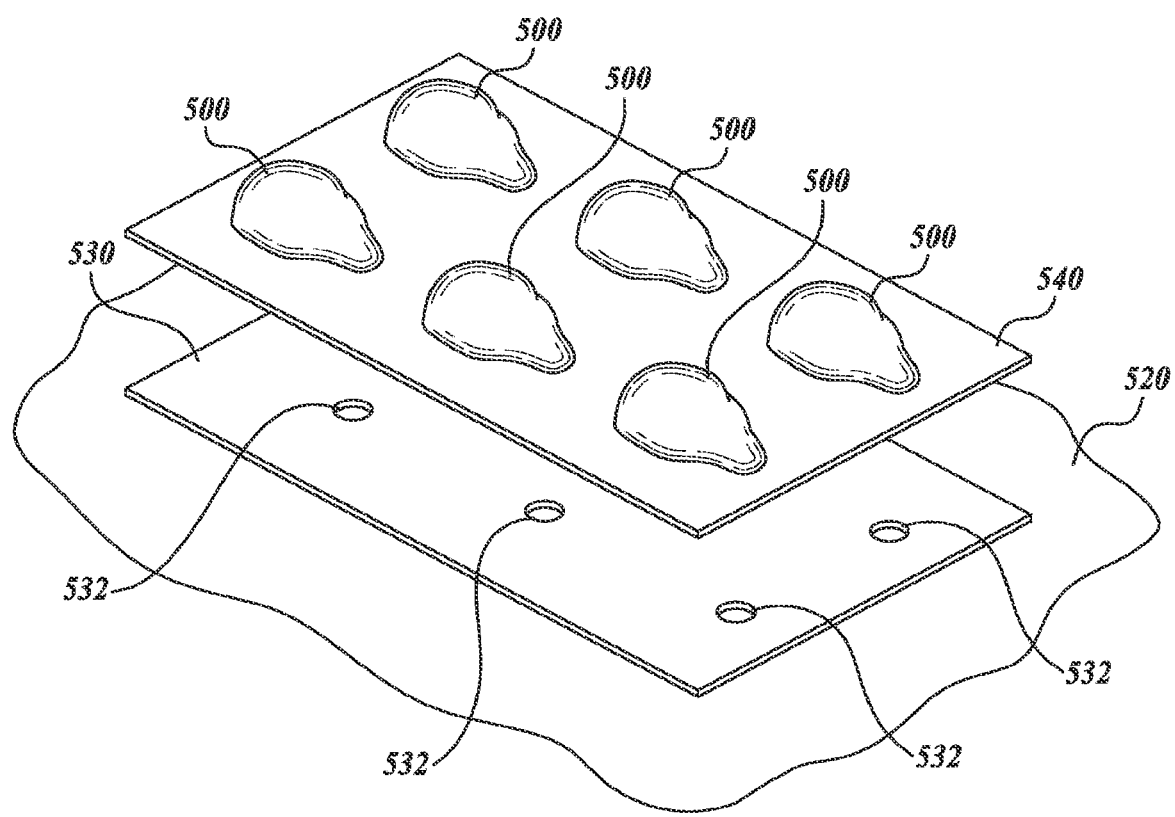
FIG. 5D depicts an exploded view of a system for use in dispensing conductive fluid from one or more reservoirs to increase electrical connectivity between a patient's skin and an electrode.

FIG. 5D depicts an exploded view of one example of a system for use in dispensing conductive fluid from one or more reservoirs 500 to increase electrical connectivity between a patient's skin 520 and an electrode 530. FIG. 5D depicts the electrode 530 located between the patient's skin 520 and a reservoir layer 540. Examples of the electrode 530 include the defibrillation electrodes 404, 408 described above with respect to FIG. 4. The electrode 530 can include a conductive fabric or other conductive material that is configured to help conduct an electric discharge from a defibrillator. In a case where the electrode 530 includes a conductive fabric, the electrode 530 can be sewn into a support structure (e.g., support structure 470) worn by the patient.

In this example, the reservoir layer 540 includes a number of reservoirs 500. The number of reservoirs 500 used in reservoir layer 540 can be any number of reservoirs. The number of reservoirs 500 can be selected based on one or more of an amount of conductive fluid contained in each reservoir 500, a size of the electrode 530, an absorption rate of the electrode 530, or any other factor. While the reservoir layer 540 depicted in FIG. 5D includes reservoirs 500, any of the other reservoirs described herein can be used in the reservoir layer 540 in place of the reservoirs 500.

As shown in FIG. 5D, the electrode 530 can be positioned between the patient's skin 520 and the reservoir layer 540. Depending on the materials used to construct the electrode 530, when conductive fluid is released from the reservoirs 500, the conductive fluid can permeate the electrode 530 up to the point of saturating the electrode 530. Some of the conductive fluid that has passed through the electrode layer 530 can contact the patient's skin 520, thereby increasing electrical connectivity between the electrode 530 and the patient's skin 520. The electrode 530 can optionally include one or more holes 532 that permit passage of the conductive fluid from one side of the electrode 530 to the other side of the electrode 530.

Figure 6A:
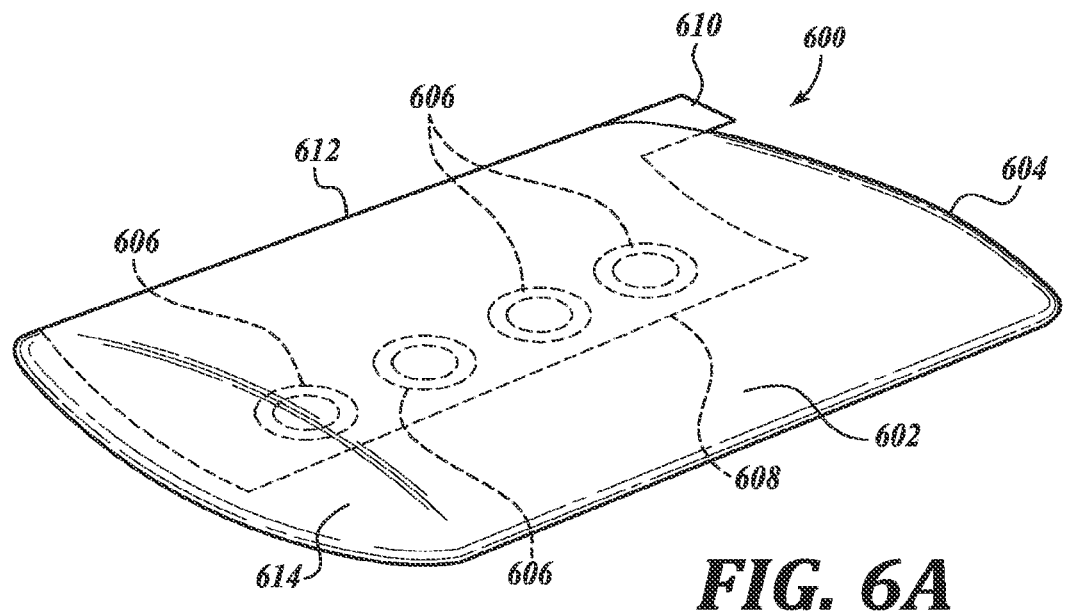
FIGS. 6A to 6E depict various views of an embodiment of a reservoir with an inflatable pouch that addresses drawbacks in the reservoir described in FIGS. 5A to 5C.
Figure 6B:
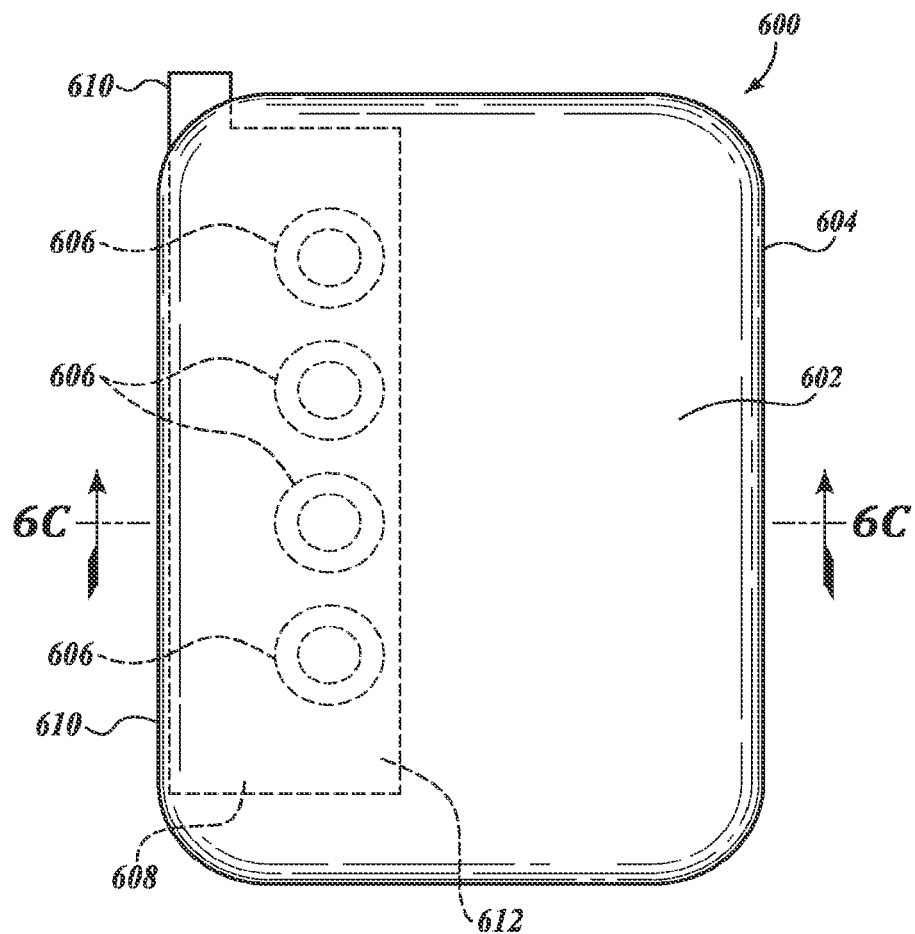
Figure 6C:
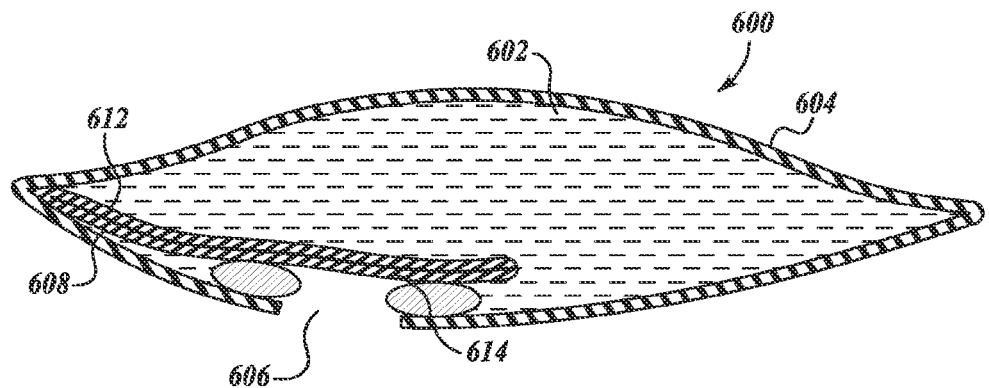
Figure 6D:
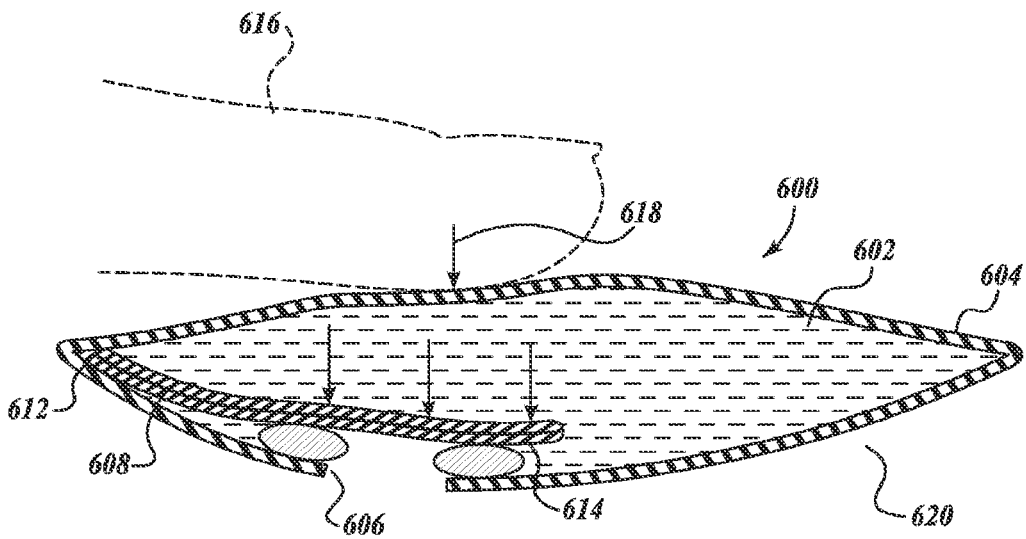
Figure 6E:
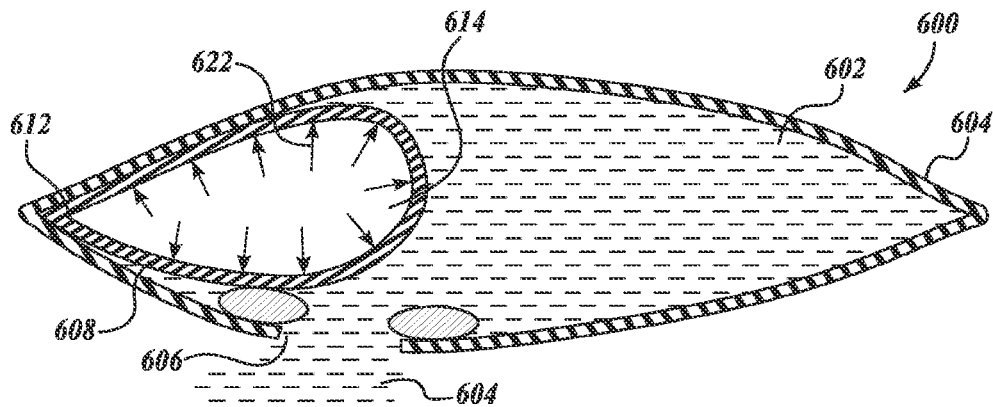

FIGS. 6A to 6E depict various views of an embodiment of a reservoir 600 that addresses drawbacks in the reservoir 500 described in FIGS. 5A to 5C. More specifically, FIGS. 6A and 6B depict perspective and top views, respectively, of the reservoir 600, and FIGS. 6C to 6E depict cross-sectional views of the reservoir 600. The reservoir 600 contains a conductive fluid 602 within a container 604. The container 604 can be a flexible container or, alternatively, a rigid or semi-rigid container. The container 604 includes one or more outlets 606 through which the conductive fluid 602 can flow. In the particular embodiment shown in FIGS. 6A and 6B, the one or more outlets 606 include four outlets arranged linearly. However, other numbers of outlets and arrangement of outlets are possible. The reservoir 600 also includes an inflatable pouch 608, at least a portion of which is located inside the container 604. The inflatable pouch 608 includes an inlet 610 through which a pressurized fluid can be forced to inflate the inflatable pouch 608. As shown in FIGS. 6A and 6B, the inlet 610 can protrude from the container 604.

The inflatable pouch 608 is depicted in a deflated state in FIGS. 6C and 6D. The inflatable pouch 608 includes a connected end 612 that is directly connected to the container 604 and a free end 614 that is not directly connected to the container 604. As shown, when the inflatable pouch 608 is in the deflated state, the free end 614 of the inflatable pouch 608 covers the one or more outlets 606. When the inflatable pouch 608 covers the one or more outlets 606, the inflatable pouch 608 prevents the conductive fluid 602 from flowing out of the container 604 via the one or more outlets 606. In at least one embodiment, the inflatable pouch 608 is sealed to the one or more outlets 606 while in the deflated state. The seal between the inflatable pouch 608 and the one or more outlets 606 can include one or more of an adhesive, a heat weld, or any other type of seal.

As shown in FIG. 6D, an object 616, such as a person's finger, can press on the container 604 causing a force 618 on the container 604. The force 618 causes a pressure 620 in the conductive fluid 602 that is exerted on the free end 614 of the inflatable pouch 608. Unlike the force from the object 512 on the flexible container 504 in FIG. 5C, the force 618 from the object 616 does not cause the free end 614 of the inflatable pouch 608 to be uncovered from the one or more outlets 606. To the contrary, the pressure 620 pushes the free end 614 of the inflatable pouch 608 toward the one or more outlets 606. In this way, the force 618 of the object 616 helps to prevent the conductive fluid 602 from leaking out of the reservoir 600.

The inflatable pouch 608 is depicted in an inflated state in FIG. 6E. To transition the inflatable pouch 608 from the deflated state depicted in FIGS. 6C and 6D to the inflated state depicted in FIG. 6E, pressurized fluid is forced into the inflatable pouch 608 via the inlet 610. The pressurized fluid can be introduced into the inlet 610 from a fluid source, such as a gas generator (e.g., a nitrogen generator) or a pressurized fluid container (e.g., a gas cylinder). As the inflatable pouch 608 inflates from the deflated state to the inflated state; the shape of the inflatable pouch 608 transitions from flat to round. The change in shape of the inflatable pouch 608 from flat to round breaks the seal between the free end 614 of the inflatable pouch 608 and the one or more outlets 606 and removes the free end 614 of the inflatable pouch 608 from the one or more outlets 606. Once the free end 614 of the inflatable pouch 608 is removed from the one or more outlets 606, the conductive fluid 602 is allowed to flow out of the container 604 via the one or more outlets 606. In the inflated state, the inflatable pouch 608 also occupies more of the volume of the container 604 than the inflatable pouch 608 takes up in the deflated state. By occupying more volume of the container 604 in the inflated state, the inflatable pouch 608 exerts a force on the conductive fluid 602 to push the conductive fluid 602 out of the container 604 via the one or more outlets 606.

In the inflated state, the pressure of the gas in the inflatable pouch 608 can be in a particular range, such as a range from about 5 psi to about 30 psi. The pressure of the gas in the inflatable pouch 608 can be selected based on one or more of a strength of the seal between the free end 614 of the inflatable pouch 608 and the one or more outlets 606, a strength of the material of the inflatable pouch 608, a strength of the material of the container 604, a viscosity of the conductive fluid 602, a size of the one or more outlets 606, and so on.

The reservoir 600 can be positioned with respect to the wearable defibrillator such that, when the conductive fluid 602 is dispensed from the one or more outlets 606, the conductive fluid is directed toward a location that will increase electrical connectivity between an electrode and the patient's skin. For example, in the case where the garment of the wearable defibrillator includes a conductive fabric between the reservoir and the patient's skin, the one or more outlets 606 can be oriented to dispense the conductive fluid 602 toward the conductive fabric. When the one or more outlets 606 are properly oriented and the pouch 608 is inflated, the conductive fluid 602 is dispensed from the container 604 such that the conductive fluid 602 will increase electrical connectivity between the electrode and the patient's skin.

The wearable defibrillator can include a monitor that monitors the patient's heart rhythms. If the wearable defibrillator determines that the patient's heart should be treated with an electrical discharge, the wearable defibrillator can cause pressurized fluid to be delivered from a source of pressurized fluid to the inflatable pouch 608 such that the inflatable pouch 608 inflates and the conductive fluid 602 is dispensed to increase electrical connectivity between the electrode and the patient's skin. After the conductive fluid 602 has been dispensed, the wearable defibrillator can deliver an electrical discharge to the patient for treatment.

With the reservoir 600 depicted in FIGS. 6A to 6E, the electrode does not need to be housed in a rigid structure to prevent accidental dispensing of conductive fluid 602 from reservoir 600. Because no additional rigid structure is needed for the reservoir 600, an electrode with the reservoir 600 can be made compliant, flexible, thin, and light weight. This leads to easier wear underneath a patient's clothing without visible bulk and with greater comfort to the patient wearing the wearable defibrillator. Such benefits lead to better compliance in patients wearing the wearable defibrillators. The ability to make the electrode and reservoir 600 compliant also leads to better contour of the electrode along the patient's skin, resulting in better contact between the electrode and any contours of the patient's skin.

Figure 7A:
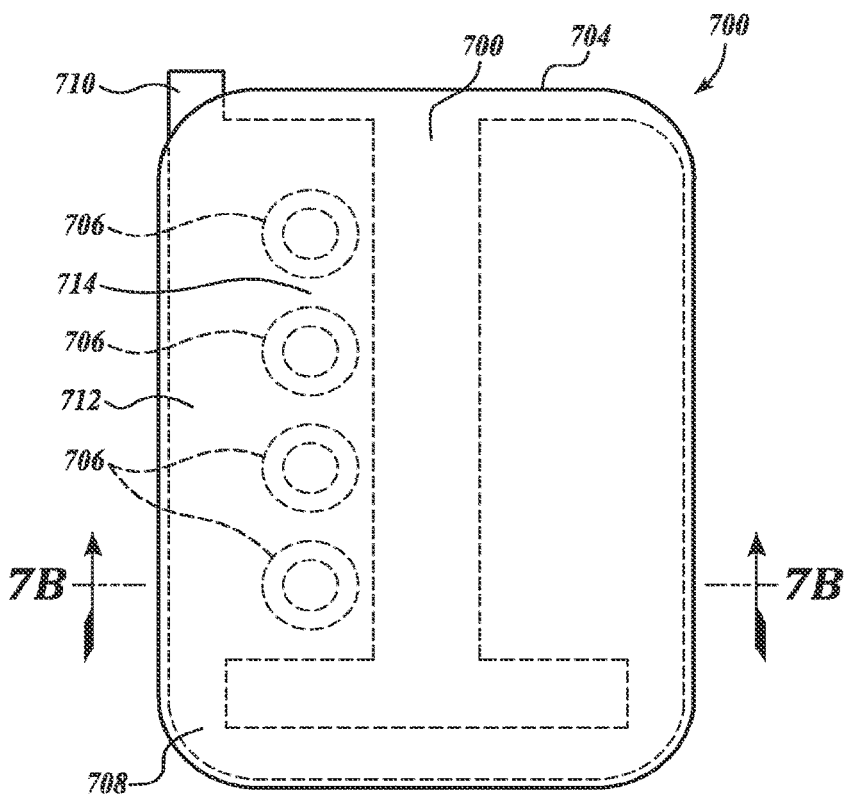
FIGS. 7A to 7C depict another embodiment of a reservoir with another embodiment of an inflatable pouch.
Figure 7B:
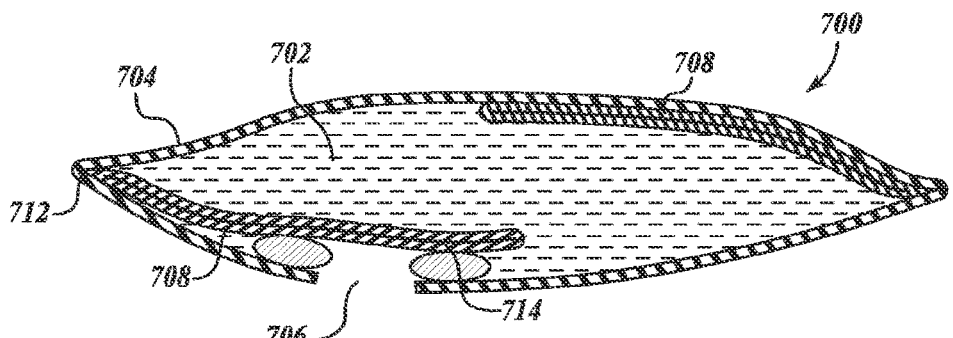
Figure 7C:
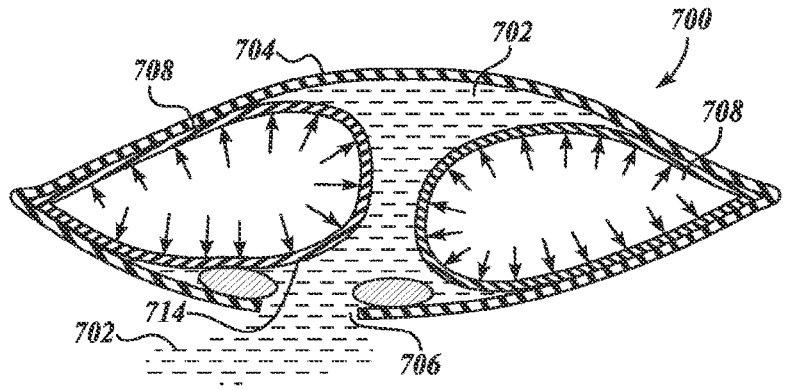

FIGS. 7A to 7C depict another embodiment of a reservoir 700 with another embodiment of an inflatable pouch 708. FIG. 7A depicts a top view of the reservoir 700 and FIGS. 7B and 7C depict cross-sectional view of the reservoir 700. The reservoir 700 contains a conductive fluid 702 within a container 704. The container 704 includes one or more outlets 706 through which the conductive fluid 702 can flow. The reservoir 700 also includes the inflatable pouch 708, at least a portion of which is located inside the container 704.

In the embodiment shown in FIG. 7A, the inflatable pouch 708 has a U-shape where the inflatable pouch 708 is located along the left side of the container 704, along the bottom side of the container 704, and along the right side of the container 704. The inflatable pouch 708 includes an inlet 710 through which a pressurized fluid can be forced to inflate the inflatable pouch 708. As shown in FIG. 7A, the inlet 710 can protrude from the container 704.

The inflatable pouch 708 is depicted in a deflated state and in an inflated state in FIGS. 7B and 7C, respectively. The inflatable pouch 708 includes a connected end 712 that is directly connected to the container 704 and a free end 714 that is not directly connected to the container 704. The cross-sectional views of the reservoir 700 in FIGS. 7B and 7C include cross-sectional views of the inflatable pouch 708 in two locations corresponding to the two sides of the U-shape of the inflatable pouch 708.

As shown in FIG. 7B, when the inflatable pouch 708 is in the deflated state, the free end 714 of the left side of the inflatable pouch 708 covers the one or more outlets 706. When the inflatable pouch 708 covers the one or more outlets 706, the inflatable pouch 708 prevents the conductive fluid 702 from flowing out of the container 704 via the one or more outlets 706. The right side of the inflatable pouch 708 is located near the top of the container 704 to provide a clear path for the conductive fluid 702 between the left and right sides of the inflatable pouch 708. In other embodiments, the right side of the inflatable pouch 708 can be located in other locations. If an object exerted a force on the top of the container 704, the left side of the inflatable pouch 708 would not be forced up and off of the one or more outlets 706.

The inflatable pouch 708 is depicted in an inflated state in FIG. 7C. To transition the inflatable pouch 708 from the deflated state depicted in FIG. 7B to the inflated state depicted in FIG. 7C, a pressurized fluid is forced into the inflatable pouch 708 via the inlet 710. The fluid can be introduced into the inlet 710 from a fluid source, such as a fluid generator (e.g., a nitrogen generator) or a pressurized fluid container (e.g., a gas cylinder). As the inflatable pouch 708 is inflated from the deflated state to the inflated state; the shape of the inflatable pouch 708 transitions from flat to round. The change in shape of the left side of the inflatable pouch 708 from flat to round breaks the seal between the free end 714 of the left side of the inflatable pouch 708 and the one or more outlets 706 and removes the free end 714 of the left side of the inflatable pouch 708 from the one or more outlets 706. Once the free end 714 of the left side of the inflatable pouch 708 is removed from the one or more outlets 706, the conductive fluid 702 is allowed to flow out of the container 704 via the one or more outlets 706.

In the inflated state depicted in FIG. 7C, the inflatable pouch 708 occupies more of the volume of the container 704 than the inflatable pouch 708 occupies in the deflated state. The U-shape of the inflatable pouch 708 also occupies more volume of the container 704 than the inflatable pouch 608 occupies in the container 604 depicted in FIG. 6E. By occupying more volume of the container 704 in the inflated state, the inflatable pouch 708 exerts a greater force on the conductive fluid 702 to push the conductive fluid 702 out of the container 704 via the one or more outlets 706. The left and right sides of the inflatable pouch 708 are arranged such that, when the inflatable pouch is in the inflated state, there is a path for most or all of the conductive fluid 702 to flow to the one or more outlets 706.

Figure 8A:
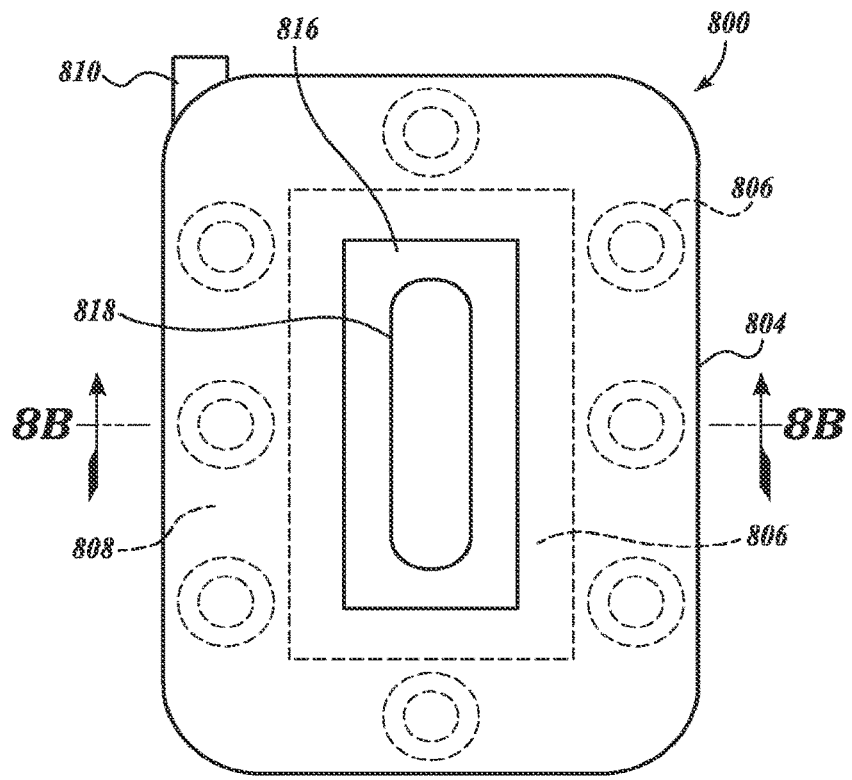
FIGS. 8A to 8C depict another embodiment of a reservoir with another arrangement of outlets and another embodiment of an inflatable pouch.
Figure 8B:
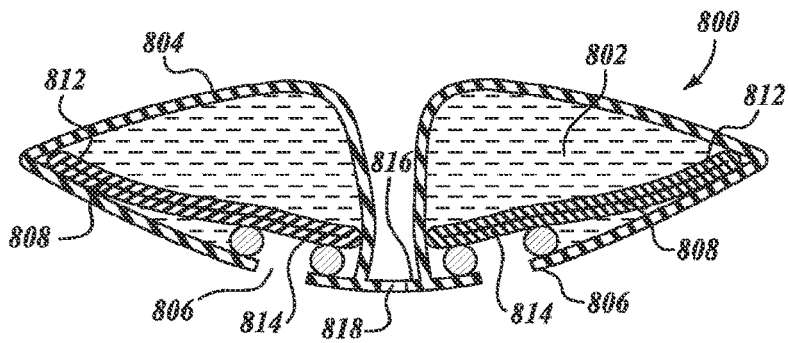
Figure 8C:
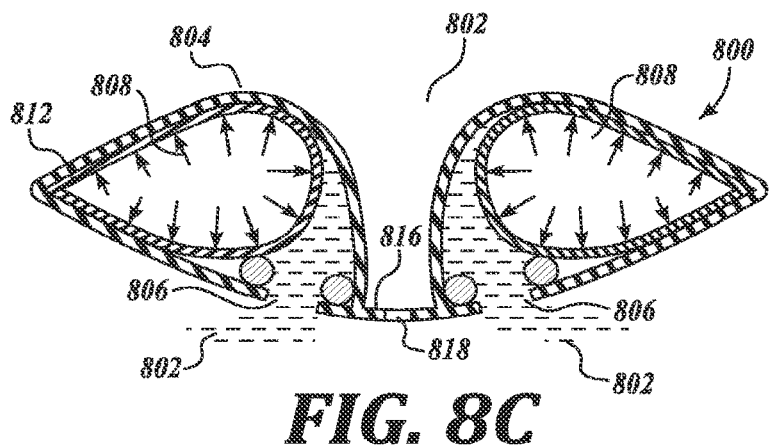

FIGS. 8A to 8C depict another embodiment of a reservoir 800 with another an arrangement of outlets 806 and another embodiment of an inflatable pouch 808. FIG. 8A depicts a top view of the reservoir 800 and FIGS. 8B and 8C depict cross-sectional view of the reservoir 800. The reservoir 800 contains a conductive fluid 802 within a container 804. The container 804 includes one or more outlets 806 through which the conductive fluid 802 can flow. In the particular embodiment shown in FIG. 8A, the one or more outlets 806 include eight outlets arranged with at least one outlet near each of the left, bottom, right, and top sides. However, other numbers of outlets and arrangement of outlets are possible. The reservoir 800 also includes the inflatable pouch 808, at least a portion of which is located inside the container 804.

The container 804 has a ring shape with a central attachment portion 816. The central attachment portion can include a hole 818. The hole can permit air to flow through the center of the container 804, making the container 804 more breathable. The inflatable pouch 808 also has a ring shape. In the particular embodiment depicted in FIG. 8A, the inflatable pouch 808 has a rectangular ring shape where the inflatable pouch 808 has sides located along the left, bottom, right, and top sides of the container 804. The inflatable pouch 808 includes an inlet 810 through which pressurized fluid can be forced to inflate the inflatable pouch 808. As shown in FIG. 8A, the inlet 810 can protrude out from the container 804.

The inflatable pouch 808 is depicted in a deflated state and in an inflated state in FIGS. 8B and 8C, respectively. The inflatable pouch 808 includes a connected end 812 that is directly connected to the container 804 and a free end 814 that is not directly connected to the container 804. The cross-sectional views of the reservoir 800 in FIGS. 8B and 8C include cross-sectional views of the inflatable pouch 808 in two locations corresponding to two sides of the rectangular ring shape of the inflatable pouch 808.

As shown in FIG. 8B, when the inflatable pouch 808 is in the deflated state, the free ends 814 of the inflatable pouch 808 covers the outlets 806. When the inflatable pouch 808 covers the outlets 806, the inflatable pouch 808 prevents the conductive fluid 802 from flowing out of the container 804 via the one or more outlets 806. The inflatable pouch 808 is depicted in an inflated state in FIG. 8C. To inflate the inflatable pouch 808 from the deflated state depicted in FIG. 8B to the inflated state depicted in FIG. 8C, a pressurized fluid is forced into the inflatable pouch 808 via the inlet 810. The fluid can be introduced into the inlet 810 from a fluid source. As the inflatable pouch 808 is inflated from the deflated state to the inflated state; the shape of the inflatable pouch 808 transitions from flat to round. The change in shape of the inflatable pouch 808 from flat to round breaks the seal between the free ends 814 of the inflatable pouch 808 and the outlets 806 and removes the free ends 814 of the inflatable pouch 808 from the outlets 806. Once the free ends 814 of the inflatable pouch 808 are removed from the one or more outlets 806, the conductive fluid 802 is allowed to flow out of the container 804 via the outlets 806.

One advantage to the reservoir 800 is depicted in FIG. 8C. When the inflatable pouch 808 is in the inflated state, both inflated sides of the inflatable pouch 808 cause the bottom of the container 804 to be pulled taught. This increases the likelihood that the sides of the inflatable pouch 808 will peel away from the outlets 806 as the inflatable pouch 808 is inflated, increasing the likelihood that the seal between the sides of the inflatable pouch 808 and the outlets 806 will break. Another advantage to the reservoir 800 is that the container 804 includes more outlets 806 than other embodiments, and that more of the conductive fluid 802 is likely to be dispensed from the reservoir with a greater the number of outlets 806. Another advantage depicted in FIG. 8C is that the central attachment portion 816 eliminates volume of the reservoir 800 that would be located in the center of the reservoir 800 if the reservoir 800 did not include the central attachment portion 816. Because of this reduced volume, the inflatable pouch 808 takes up a greater portion of the volume of the reservoir 800 in the inflated state. Because the inflatable pouch 808 takes up a greater portion of the volume of the reservoir 800 in the inflated state, inflation of the inflatable pouch 808 will cause more of the conductive fluid 802 to flow out of the outlets 806 than if the reservoir 800 did not include the central attachment portion 816.

FIG. 9 depicts an embodiment of a free end 914 of an inflatable pouch 908 that can be used with any of the embodiments of inflatable pouches described herein. FIG. 9 depicts a reservoir 900 that contains a conductive fluid 902 within a container 904. The container 904 includes outlets 906. The reservoir 900 also includes the inflatable pouch 908, at least a portion of which is located inside the container 904. In the embodiment shown in FIG. 9, the inflatable pouch 908 has free end 914 with a saw-tooth shape. The inflatable pouch 908 includes an inlet 910 through which fluid can be forced to inflate the inflatable pouch 908.

The saw-tooth shape of the free end 914 of the inflatable pouch 908 includes valleys 924 and peaks 926. Individual valleys 924 are located near individual outlets 906 and individual peaks 926 are located between two of the outlets 906. As the inflatable pouch 908 is inflated, the portion of the free end near the valleys 924 is more likely to pull away from the container 904. Thus, the free end 914 of the inflatable pouch 908 is more likely to peel away from the outlets 906 when the valleys 924 of the free end 914 are located near the outlets 906.

FIG. 10 depicts an embodiment of a system 1000 that can be used with any of the conductive fluid reservoirs described herein. The system 1000 includes a controller 1002 that is communicatively coupled to a first gas generator 1004 and a second gas generator 1006. While gas generators 1004, 1006 generating pressurized gas are shown in this embodiment, alternatively other forms of fluid generators or fluid sources may be used to supply pressurized fluid to pouches disposed within the conductive fluid reservoirs 1008, 1012. The first gas generator 1004 is configured to selectively provide a pressurized gas via fluid channels 1006 to each of one or more conductive fluid reservoirs 1008 that are associated with a first electrode (not shown). The second gas generator 1006 is configured to selectively provide a pressurized gas via fluid channels 1010 to each of one or more conductive fluid reservoirs 1012 that are associated with a second electrode (not shown). In the embodiment shown in FIG. 10, the conductive fluid reservoirs 1008 include three conductive fluid reservoirs and the conductive fluid reservoirs 1012 include three conductive fluid reservoirs. However, the conductive fluid reservoirs 1008 and 1012 can have other numbers of conductive fluid reservoirs. For example, without limitation, a group of four or five conductive fluid reservoirs can be associated with each electrode. Moreover, the conductive fluid reservoirs 1008 and 1012 can have different numbers of conductive fluid reservoirs, such as conductive fluid reservoirs 1008 having four conductive fluid reservoirs and conductive fluid reservoirs 1012 having five conductive fluid reservoirs.

As noted above, in at least one embodiment, the first gas generator 1004 and the conductive fluid reservoirs 1008 are associated with a first electrode, and the second gas generator 1006 and the conductive fluid reservoirs 1012 are associated with a second electrode. For example, the first electrode, the first gas generator 1004, and the conductive fluid reservoirs 1008 can be part of a first electrode assembly, and the second electrode, the second gas generator 1006, and the conductive fluid reservoirs 1012 can be part of a second electrode assembly. The first and second electrodes can be positioned in a wearable defibrillator to be able to deliver an electric charge to a patient's heart. The controller 1002 can be a part of or coupled to a monitor (e.g., monitoring device 480 shown in FIG. 4) that monitors the rhythm of the patient's heart.

The monitor can monitor the patient's heart using electrodes on the patient that are different from the first and second electrodes (e.g., using monitoring electrodes that do not require a conductive fluid to effectively monitor the patient's heart rhythm). When the monitor detects an arrhythmia, the controller 1002 can send signals to the first gas generator 1004 and the second gas generator 1006 indicating that conductive fluid should be dispensed from the conductive fluid reservoirs 1008 and 1012. In response to receiving the signals from the controller 1002, the first gas generator 1004 can deliver pressurized gas via the fluid channels 1006 to the conductive fluid reservoirs 1008 and the second gas generator 1006 can deliver pressurized gas via the fluid channels 1010 to the conductive fluid reservoirs 1012. The pressurized gas delivered to the conductive fluid reservoirs 1008 and 1012 can inflate inflatable pouches within the conductive fluid reservoirs 1008 and 1012 to remove free ends of the inflatable pouches from outlets such that conductive fluid flows out of the conductive fluid reservoirs 1008 and 1012. The conductive fluid from the conductive fluid reservoirs 1008 can be directed to increase electrical connectivity between the first electrode and the patient's skin, and the conductive fluid from the conductive fluid reservoirs 1012 can be directed to increase electrical connectivity between the second electrode and the patient's skin. Once the conductive fluid flows out of the conductive fluid reservoirs 1008 and 1012, the wearable defibrillator can effectively deliver an electrical discharge to the patient's heart between the first and second electrodes to treat the arrhythmia.

FIG. 11 depicts an embodiment of a method 1100 for preparing a patient for defibrillation treatment using any of the conductive fluid reservoirs describe herein. At block 1102, a patient's heart rhythm is monitored. The patient's heart rhythm can be monitored by a monitor in a wearable defibrillator-monitor. The patient's heart rhythm can be monitored using electrodes that are different from electrodes that will be used to deliver an electric charge to treat any arrhythmia of the patient's heart. At block 1104, an arrhythmia of the patient's heart can be detected. Detecting the arrhythmia can include making a determination that the arrhythmia requires delivery of an electric charge to the patient's heart for treatment of the arrhythmia.

At block 1106, conductive fluid is dispensed from conductive fluid reservoirs to increase electrical connectivity between one or more electrodes and the patient's skin. The conductive fluid can be dispensed from the conductive fluid reservoirs by causing pressurized fluid to inflate inflatable pouches in the conductive fluid reservoirs such that free ends of the inflatable pouches are removed from outlets of the conductive fluid reservoirs and the conductive fluid is permitted to flow out of the conductive fluid reservoirs via the outlets. The pressurized fluid can be caused to inflate inflatable pouches in the conductive fluid reservoirs by a controller sending a signal to one or more gas generators that are configured to deliver the pressurized fluid to the conductive fluid reservoirs. The pressurized fluid can be delivered to inflate inflatable pouches in the conductive fluid reservoirs in other ways, such as by opening a valve between a source of pressurized fluid and the conductive fluid reservoirs. At block 1108, an electrical discharge is delivered to the patient's heart via the one or more electrodes and the dispensed conductive fluid.

FIGS. 12A, 12B, 13A, and 13B depict embodiments of conductive fluid reservoirs in the form of pressurized balloons. The pressurized balloons can be used to dispense a conductive fluid to increase electrical connectivity between an electrode and the patient's skin. The conductive fluid can be stored under pressure in the balloon such that, when the balloon is opened, the conductive fluid automatically dispenses out of the balloon. The balloon can be located and/or oriented such that the conductive fluid is directed to increase electrical connectivity between an electrode and the patient's skin when the balloon is opened.

Figure 12A:
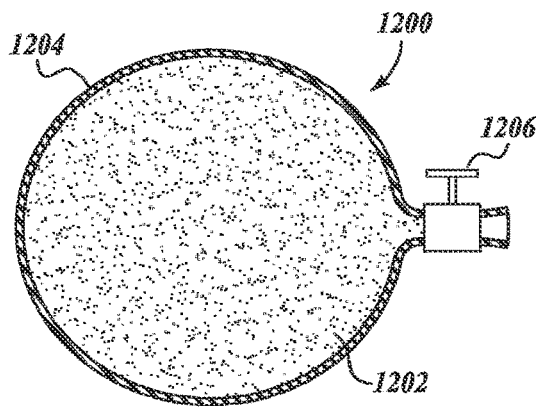
FIGS. 12A and 12B depict an embodiment of a conductive fluid reservoir that includes a pressurized balloon and a release valve.
Figure 12B:
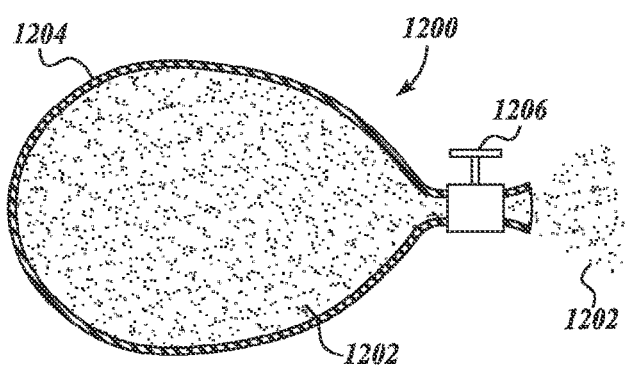

FIGS. 12A and 12B depict an embodiment of a conductive fluid reservoir 1200 that includes a pressurized balloon 1204. The pressurized balloon 1204 contains a conductive fluid 1202. The pressurized balloon 1204 includes a release valve 1206 that can be selectively opened to allow some or all of the conductive fluid 1202 out of the pressurized balloon 1204. FIG. 12A depicts the release valve 1206 in a closed position and FIG. 12B depicts the release valve 1206 in an open position with the conductive fluid 1202 flowing out of the pressurized balloon 1204.

The release valve 1206 can be controlled by the wearable defibrillator such that the release valve 1206 is opened automatically before the wearable defibrillator delivers an electrical discharge to the patient's body. Furthermore, using the release valve 1206 with the pressurized balloon 1204 may allow the pressurized balloon 1204 to be refilled with additional conductive fluid and reused. The release valve 1206 can be oriented such that the conductive fluid 1202 is directed to increase electrical connectivity between an electrode of the wearable defibrillator and the patient's skin when the release valve 1206 is opened.

Figure 13A:
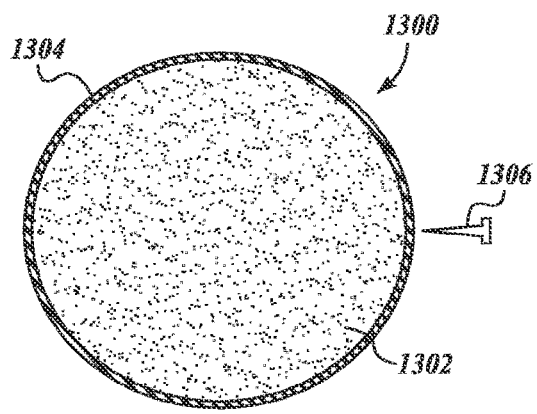
FIGS. 13A and 13B depict an embodiment of a conductive fluid reservoir that includes a pressurized balloon that can be punctured using a puncturing device.
Figure 13B:
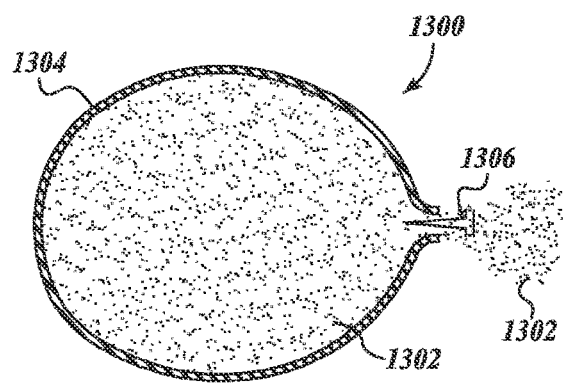

FIGS. 13A and 13B depict an embodiment of a conductive fluid reservoir 1300 that includes pressurized balloon 1304. The pressurized balloon 1304 contains a conductive fluid 1302. The pressurized balloon 1304 can be opened by puncturing the pressurized balloon 1304. The pressurized balloon 1304 can be punctured using a puncturing device 1306, such as a pin, a blade, and the like. FIG. 13A depicts the pressurized balloon 1304 before being punctured by the puncturing device 1306 and FIG. 13B depicts the pressurized balloon 1304 after being punctured by the puncturing device 1306 with the conductive fluid 1302 flowing out of the pressurized balloon 1304.

The puncturing device 1306 can be controlled by the wearable defibrillator such that the pressurized balloon 1304 is punctured automatically before the wearable defibrillator delivers an electrical discharge to the patient's body. The puncturing device 1306 can be oriented such that the conductive fluid 1302 is directed to increase electrical connectivity between an electrode of the wearable defibrillator and the patient's skin when the pressurized balloon 1304 is punctured.

Any of the pressurized balloon embodiments described herein can be contained in a rigid container in the wearable defibrillator. The rigid container can prevent inadvertent rupturing of the balloon while the patient wears the wearable defibrillator.

It should be noted that for purposes of this disclosure, the use of "including," "comprising," or "having" and variations thereof herein is meant to encompass the items listed thereafter and equivalents thereof as well as additional items. Unless limited otherwise, the terms "connected" and "coupled" and variations thereof herein are used broadly and encompass direct and indirect connections and couplings.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. A conductive fluid dispenser for use with an electrotherapy system, the device comprising:
    a reservoir layer;
    a plurality of reservoirs disposed on the reservoir layer, each of the plurality of reservoirs comprising a pouch disposed within a volume of a conductive fluid, wherein at least one of the plurality of reservoirs surrounds a seal;
    a controller connected to at least one reservoir in the plurality of reservoirs, the controller configured to control selective delivery of a pressurized fluid to increase a pressure inside the at least one reservoir; and
    at least one conductive surface configured to come into contact with the conductive fluid when the pouch expands responsive to the increased pressure inside the at least one reservoir so that the conductive fluid evacuates from the at least one reservoir, the conductive surface configured to transfer a therapeutic current to a body of a patient,
    wherein a source of the pressurized fluid comprises one of either a gas generator, a pressurized fluid container, or a combination of gas generator and pressurized fluid container.

2. The conductive fluid dispenser of claim 1, further comprising:
    an inlet of the at least one reservoir connected to the source of pressurized fluid to deliver the pressurized fluid.

3. The conductive fluid dispenser of claim 2, wherein the source of the pressurized fluid is fluidly coupled to the inlet of the at least one reservoir or directly to the volume of the conductive fluid.

4. The conductive fluid dispenser of claim 1, further comprising:
    one or more outlets disposed on the at least one reservoir to release the conductive fluid to the at least one conductive surface.

5. The conductive fluid dispenser of claim 3, further comprising:
    a fluid conduit formed between the inlet and the one or more outlets to flow the conductive fluid to the one or more outlets when the pressurized fluid flows into the at least one reservoir.

6. The conductive fluid dispenser of claim 1, wherein the increased pressure inside of the at least one reservoir breaks the seal on the pouch to release the conductive fluid to the at least one conductive surface.

7. The conductive fluid dispenser of claim 1, wherein the source of the fluid pressure is removably coupled to the at least one reservoir.

8. The conductive fluid dispenser of claim 1, wherein the one or more outlets are arranged linearly.

9. A conductive fluid reservoir, comprising:
    a reservoir layer;
    a reservoir disposed on the reservoir layer comprising a pouch and a volume of a conductive fluid, wherein the pouch surrounds a seal; and
    at least one conductive surface configured to come into contact with the conductive fluid when the seal is broken so that the conductive fluid evacuates from the reservoir, the conductive surface configured to transfer a therapeutic current to a body of a patient.

10. The conductive fluid reservoir of claim 9, further comprising:
    a controller connected to the reservoir, the controller configured to control selective delivery of a pressurized fluid to increase a pressure inside the reservoir to break the seal.

11. The conductive fluid reservoir of claim 10, further comprising:
    a source of the pressurized fluid is removably coupled to the reservoir.

12. The electrode system of claim 11, wherein the source of pressurized fluid is a gas generator.

13. The electrode system of claim 11, wherein the source of pressurized fluid is a pressurized fluid container.

14. An electrode system comprising:
    a gel deployment receptacle configured to release a conductive gel onto a body of a subject, the gel deployment receptacle includes a container defining a gel reservoir and a pouch disposed within the gel reservoir, the gel reservoir comprises the conductive gel, the pouch surrounds a seal; and
    a fluid source in fluid communication with the gel deployment receptacle.

15. The electrode system of claim 14, wherein
    a controller connected to the gel reservoir, the controller configured to control selective delivery of a pressurized fluid to increase a pressure inside the gel reservoir to break the seal.

16. The electrode system of claim 14, further comprising:
    the fluid source is removably coupled to the reservoir.

17. The electrode system of claim 14, wherein
    the fluid source comprises one of either a gas generator, a pressurized fluid container, or a combination of gas generator and pressurized fluid container.

18. The electrode system of claim 14, wherein
the electrode system is disposed within a wearable defibrillator device and comprises a plurality of therapy electrodes configured to deliver at least one of defibrillation shocks to the subject wearing the wearable defibrillator device.

19. The electrode system of claim 14, wherein the fluid source is a gas generator.

20. The electrode system of claim 14, wherein the fluid source is a pressurized fluid container.

* * * * *